United States Patent
Chen

(10) Patent No.: US 6,309,555 B1
(45) Date of Patent: Oct. 30, 2001

(54) METHOD FOR DETERMINING THICKNESS OF MATERIAL LAYER AND CHEMICAL MECHANICAL POLISHING ENDPOINT

(75) Inventor: Hsueh-Chung Chen, Taipei Hsien (TW)

(73) Assignee: United Microelectronics Corp., Hsinchu (TW)

(*) Notice: Subject to any disclaimer, the term of this patent is extended or adjusted under 35 U.S.C. 154(b) by 0 days.

(21) Appl. No.: 09/260,202

(22) Filed: Mar. 1, 1999

(51) Int. Cl.[7] .............................. B44C 1/22; C03C 15/00; C23F 1/00
(52) U.S. Cl. ................. 216/85; 216/84; 438/14; 438/16; 451/6
(58) Field of Search .................. 216/84, 85; 438/14, 438/16; 451/6

(56) References Cited

U.S. PATENT DOCUMENTS

| | | | |
|---|---|---|---|
| 4,454,001 | * 6/1984 | Sternheim et al. | 216/85 |
| 4,998,021 | * 3/1991 | Mimasaka | 216/85 |
| 5,695,601 | * 12/1997 | Kodera et al. | 216/85 |
| 6,010,538 | * 1/2000 | Sun et al. | 756/345 |
| 6,024,628 | * 2/2000 | Chen | 451/5 |

* cited by examiner

*Primary Examiner*—Randy Gulakowski
*Assistant Examiner*—Shamim Ahmed
(74) *Attorney, Agent, or Firm*—Thomas, Kayden, Horstemeyer & Risley, LLP

(57) ABSTRACT

A method for real-time detecting the thickness of a material layer. A reflected light is measured of an incident light emitted toward the material layer. By integrating the intensity of the reflected light along the time axis, followed by dividing by the product of the derivative of the intensity of the reflected light and the polishing time, an I-Dt transformation curve can be obtained. Since the I-Dt transformation curve has characteristics associated with a cosecant function, which has salient peaks on the curve, the thickness of the material layer can be real-time determined. Furthermore, due to the facts that the transformed curve has salient peaks, the function itself reveals the sign of the slope, and the transformed curve are relatively flat between peaks, correct and stable rules can therefore be provided to determine the analytical endpoint.

4 Claims, 2 Drawing Sheets

METHOD FOR DETERMINING THICKNESS OF MATERIAL LAYER AND CHEMICAL MECHANICAL POLISHING ENDPOINT

BACKGROUND OF THE INVENTION

1. Field of the Invention

The present invention generally related to a method for determining a real-time thickness of a single material layer, and more particularly to a method for determining an endpoint for a chemical-mechanical polishing (CMP) process.

2. Description of the Related Art

Chemical-mechanical polishing (CMP) is currently regarded as the only technology to provide global planarization in fabricating very-large scale integrated (VLSI) circuits, or even ultra-large scale integrated (ULSI) circuits. Essentially, the CMP is based on a principle similar to a "polishing wheel" in mechanical polishing. With the aid of a reagent, the rough surface of a wafer can then be smoothly ground by using this technology.

As the technologies of fabricating semiconductor devices enter the deep sub-micron regime, the CMP has become a conventional technology in fabricating ICs, in which an endpoint detection (EDP) method is the most critical factor in extending process window during the CMP process and overcoming stability problem in mass production.

To perform the endpoint detection for a dielectric layer, optical methods are the most popular ones, which measure the intensity of a reflected light as a function of time. Working together with the "Window Logic", turning-around points of slope on the curve can be identified, so that the endpoint of the CMP process can be determined. This method has advantages of real-time detection, no direct contact, and less noise induced.

The following paragraph describes the principles on which the endpoint detection method is based. Problems associated with this method are also described hereinafter.

Referring to FIG. 1, a light $I_{inc}$ is incident onto a dielectric layer 10. Being reflected from the top surface of the dielectric layer 10, and an interface between the dielectric layer 10 and an underlying substrate 12, the intensity of a reflected light I can be obtained from principles of optical interference:

$$I = I_A + I_B + 2\sqrt{I_A I_B} \cos\phi \qquad (1)$$

$$\phi = \frac{4\pi n d}{\lambda_0 \cos(\alpha_{ref})}$$

and I is the intensity of a reflected light, t is the time, $I_A$ is the intensity of the first reflected light, $I_B$ is the intensity of the secondary reflected light, n is the refraction index of the material layer, d is the thickness of the material layer, $\lambda_0$ is the wavelength of the incident light, $\alpha_{ref}$ is the refractive angle.

Eq. (1) shows that the intensity of the reflected light versus polishing time (I-t curve) comprises a cosine function as shown in FIG. 2. However, neither the thickness nor the endpoint of the process can be obtained from Eq. (1), unless a correlation between the intensity curve and the dielectric layer thickness was established. Consequently, it is very different to detect the endpoint of a CMP process on which applied to a single dielectric layer, for example, inter-layer dielectric (ILD) or shallow trench isolation (STI), since there is no strong signal difference coming from the interfaces of two different materials. Thus, the endpoint of the CMP process needs to be determined depending on the periodical variation of I-t curve.

For $\phi = m\pi, m = 0, 1, 2, \ldots$, the corresponding thickness $d_m$ can be obtained by $$d_m = \frac{m \lambda_0 \cos(\alpha_{ref})}{4n} \qquad (2)$$

the peaks and valleys on the I-t curve correspond to a certain thickness provides the initial thickness of the dielectric layer is know. Referring to and I-t curve obtained from polishing the whole thickness of a layer, these peaks and valleys form a set of characteristic points or indices, which can be used to determine the endpoint of the CMP process.

As shown in FIG. 2, a local minimum point 202 on the curve which is closest to the desired endpoint of a CMP process can be obtained, which is called the "analytical endpoint" 204 because it can be explicitly defined on the curve. This local minimum point 202 can be identified by "window logic", as it is the changing point of slope. After reaching the analytical endpoint 204, an over polishing step is further performed until reaching a required final thickness 206.

Thus, for a single dielectric layer (ILD) or a shallow trench isolation (STI) CMP process, the conventional endpoint detection technology identifies several local maximum/minimum points on the curve which have a thickness close to the desired thickness based on wavelength of the incident light.

However, there are still some problems for the above-mentioned principle to be applied practically. Although the peaks and valleys refers to a certain thickness are those identified with a slope of zero on the curve, it is not easy, however, to have an accurate calculation for these points because of the constraint on the speed of the polishing table. For example, sampling rate in a CMP process is generally only 1 sample/second due to a reasonable process parameter, which is not sufficient to accurately identify points with a zero slope. A more practical way to identify the peaks and valleys with zero slope is through the turning-around points on the curve by identifying changes between positive and negative slopes. FIG. 2 shows a conventional "window logic" method to determine the analytical endpoint, in which observing windows 208 are used to identify the turning-around points on the curve. This method has an advantage of simplicity, but associated accuracy and reoccurrence are not so good. To minimize errors that might occur due to noises and interference on the curve, consecutive three to four windows are normally required to define a turn-around point. The inaccuracy of this method therefore guarantees no successful results in detecting peaks and valleys on the curve.

Due to different material used, environmental and process variations, problems encountered so far toward mass production includes that the thickness determination may not reflect the true thickness accurately since signals varies upon polishing material. In addition, the CMP processes demanding a very short polishing time, especially those having a polishing time of less than a signal period, the conventional method is not applicable. Furthermore, the corresponding I-t curves for each wafer can be dirrerent in both amplitude and period, because of difference in wafer and environment. Usually, different endpoint thickness is required for different processes, so that the corresponding endpoint on the I-t curve is different. Therefore, feasible rules need to be established to solve these problems.

The reason behind the above-mentioned problems is that the conventional signal analysis technology fails to accurately identify the peaks and valleys on I-t curve. The conventional method fails to quickly and correctly identify the slope of a point on the curve, whether it is descending or ascending.

SUMMARY OF THE INVENTION

It is therefore an objective of the present invention to provide a method for accurately identifying the peaks and valleys of intensity of the reflected light on the I-t curve, so that the thickness of the dielectric layer can be detected.

It is another objective of the present invention to provide a method for quickly and correctly determining whether the slope on the curve of the intensity of the reflected light is descending or ascending, so that the accuracy in detecting the dielectric layer can be improved.

It is another objective of the present invention to provide a method to overcome the problems mentioned earlier so that the endpoint detection method can be used in mass production processes.

In accordance with the foregoing and other objectives of the present invention, a method for real-time determining the thickness of a material layer is provided. The thickness of the material layer on a substrate decreases as time elapses. A reflected light is measured by using an incident light emitted toward the material layer. By integrating the intensity of the reflected light along the time axis, followed by being divided by the product of the derivative of the intensity of the reflected light and the polishing time, and I-Dt transformation curve is thus obtained. Since the I-Dt transformation curve has characteristics associated with a cosecant function, which has salient peaks on the curve, the thickness of the material layer can be real-time determined.

In accordance with the foregoing and other objectives of the present invention, a method for determining the endpoint with desired thickness during a CMP process is provided. When the CMP process is undertaking, a reflected light is measured by using an incident light emitted toward the material layer. By integrating the intensity of the reflected light along the time axis, followed by being divided by the product of the derivative of the intensity of the reflected light and the polishing time, an I-Dt transformation curve is therefore obtained. Since the I-Dt transformation curve has characteristics associated with a cosecant function, which has salient peak values on the curve, the thickness of the material layer can be real-time determined. Therefore, the endpoint with the desired thickness can be determined.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
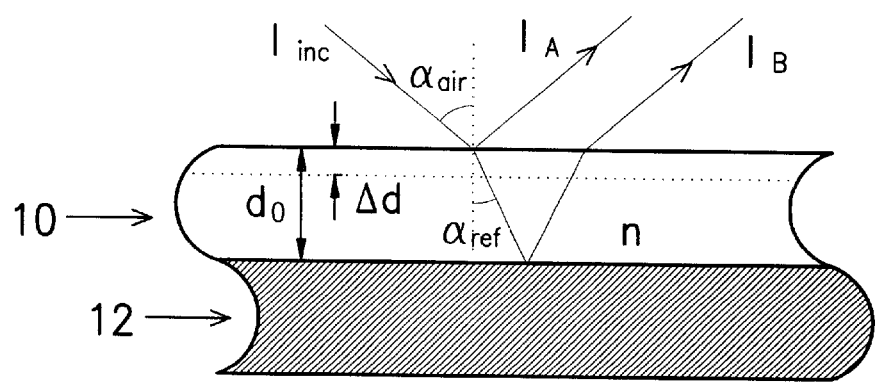
FIG. 1 is a schematic diagram showing a conventional optical method to detect the endpoint of a dielectric layer during a CMP process.

Reference will now be made in detail to the present preferred embodiments of the invention, examples of which are illustrated in the accompanying drawings. Wherever possible, the same reference numbers are used in the drawings and the description to refer to the same or like parts.

Figure 2:
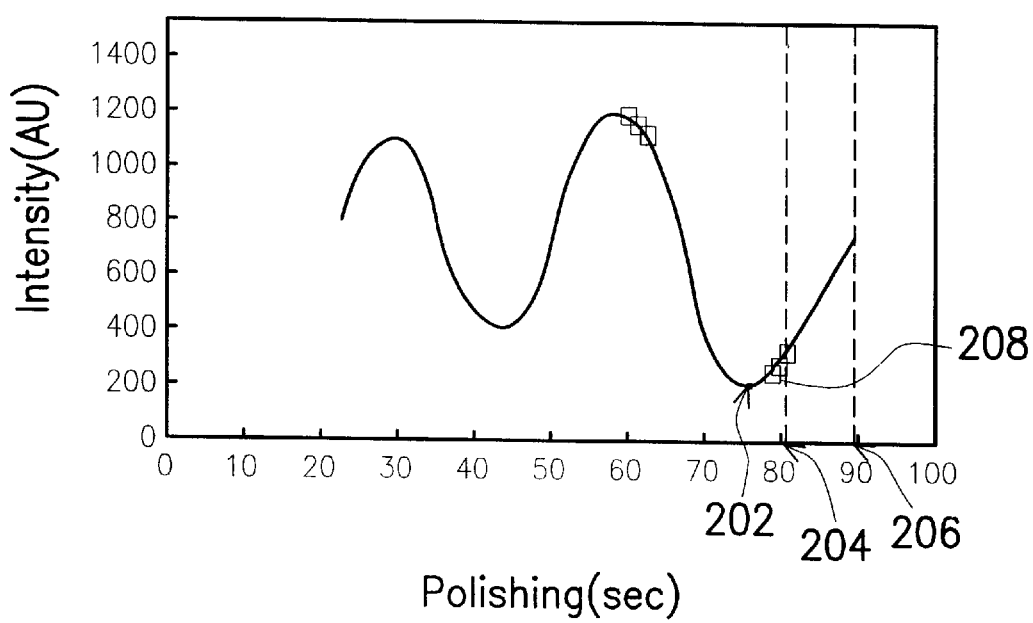
FIG. 2 is a schematic diagram of the intensity of the reflected light versus polishing time, based on which the endpoint with desired thickness is determined.
Figure 3:
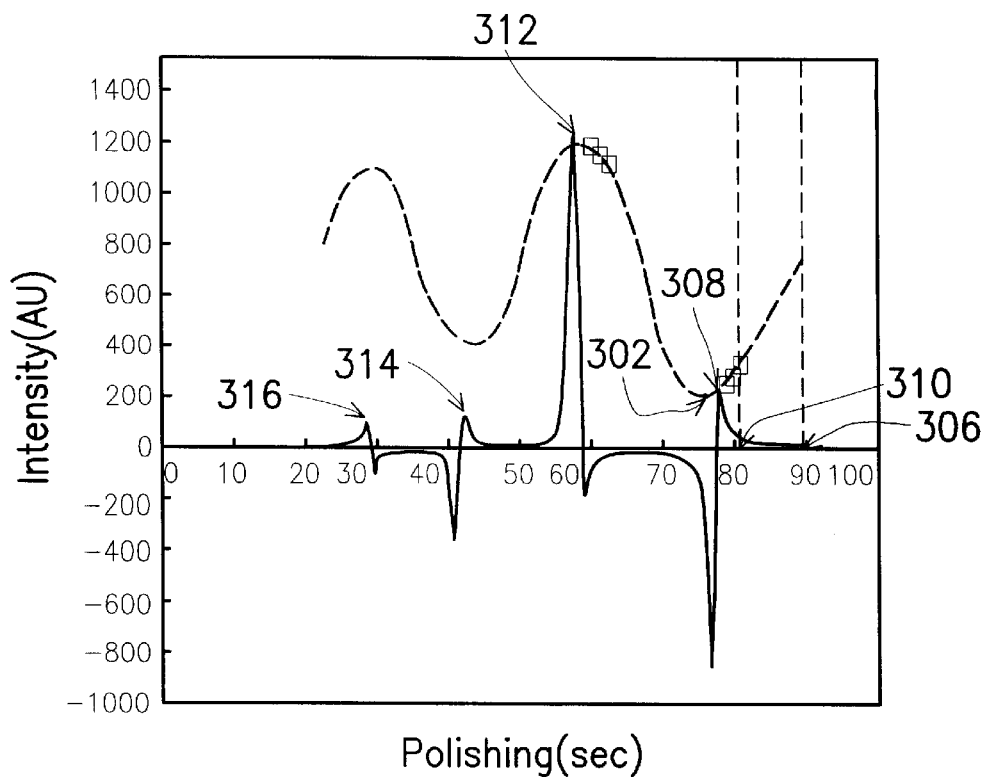
FIG. 3 is a schematic diagram of the I-Dt transformation curve where the intensity of the reflected light is integrated along the time axis and divided by the product of the derivative of the intensity of the reflected light and the polishing time according to one preferred embodiment of the present invention.

The following paragraph describes the principles on which the present invention is based as well as the improvements over the conventional methods. The intensity of the reflected light is integrated along the time axis. The integration of the intensity of the reflected light is then divided by the product of the derivative of the intensity of the reflected light and the polishing time to obtain a so-called I-Dt transformation. The I-Dt transformation is drawn as a diagram as shown in FIG. 3 in comparison with the I-t curve shown in FIG. 2. The intensity of the reflected light transformed by the I-Dt transformation can be described as:

$$\frac{\int I dt}{I' \cdot t} = -\frac{(I_A + I_B)}{2\sqrt{I_A + I_B}} \csc(\phi) \frac{dt}{d\phi} - \frac{1}{t}\left(\frac{dt}{d\phi}\right)^2 \quad (3)$$

where $$\phi = \frac{4\pi n d}{\lambda_0 \cos(\alpha_{ref})}$$

and I is the intensity of the reflected light, t is the time, $I_A$ is the intensity of the first reflected light, $I_B$ is the intensity of the secondary reflected light, n is the refraction index of the material layer, d is the thickness of the material layer, $\lambda_O$ is the wavelength of the incident light, $\alpha_{ref}$ is the refractive angle.

Note that $$\frac{dt}{d\phi}$$

in Eq. (3) is a constant, therefore, the second term on the right hand side of Eq. (3) is negligible as time increases. The first term on the right hand side of Eq. (3) becomes the dominant factor. That is, the transformed curve has characteristics associated with a cosecant function as shown in FIG. 3. It is understood that the transformed curve comprises the advantages:

1. Peaks and valleys on the I-Dt transformation curve are salient and easily identified. The problems encountered to identify the peaks by using the conventional methods are then overcome. Since the derivative term is in the denominator, peaks are explicitly formed on the curve at peaks and valleys, which can be accurately identified. For example, a peak is identified on the curve in FIG. 3 to be the analytical endpoint. The analytical endpoint obtained from the I-Dt transformation curve are very close to the extreme point obtained from the I-t curve with an excellent accuracy. Compared with the conventional methods, the present invention no longer requires the window logic to use consecutive three to four windows to determine a turn-around point on the conventional I-t curve. Furthermore, the peaks on the I-Dt transformation curve corresponds to the peaks and valleys on the I-t curve according to one preferred embodiment of the present invention.

2. The transformed function itself reveals the sign of the slope on the curve, either positive or negative. Therefore, inaccurate problems in the conventional methods are then overcome. Since the integral term is a monotonically increasing function, therefore the derivative term determines whether the transformed function is positive or negative. That is, the transformed function itself reveals the sign of the slope. Whether points on the I-Dt transformation curve is ascending or descending can be quickly and correctly determined.

Figure 4:
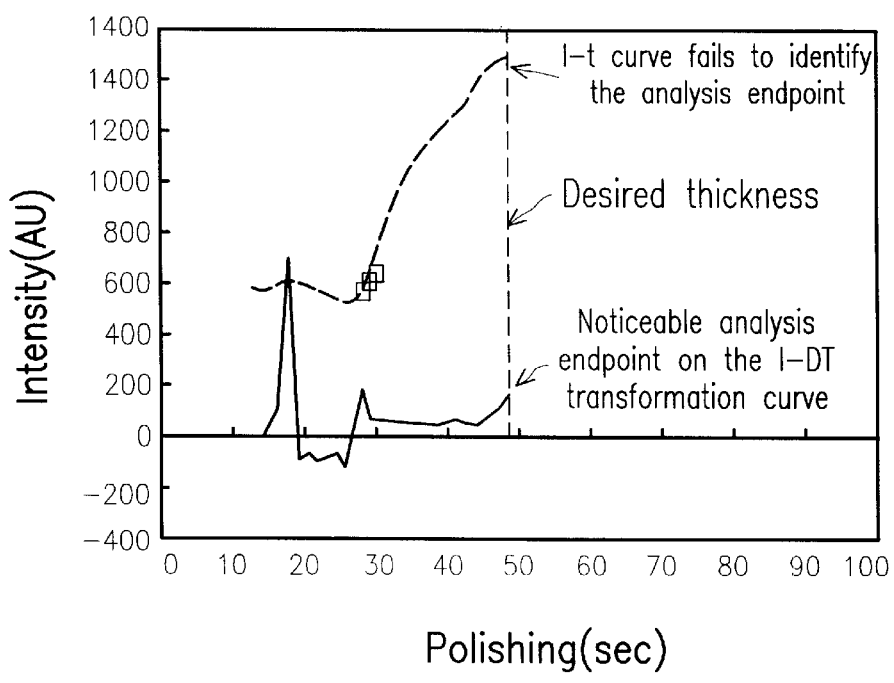
FIG. 4 is a schematic diagram of the I-Dt transformation curve in analyzing a short polishing time CMP process according to one preferred embodiment of the present invention.

3. Twice of signal characteristics are provided in analyzing a short polishing time process, especially for processes having a polishing time of less than a complete periodic cycle. Since the slope on the I-t curve from $\phi=m\pi$ to $\phi=(m+1)\pi$ is the same, the conventional method (I-t curve) fails to accurately identify peaks within this interval. However, by using the transformed curve (I-Dt transformation curve), there are two peaks identified within this interval as shown in FIG. 4. Therefore, for a short polishing time process of less than a periodic cycle, more information can be provided by the I-Dt transformation.

4. A broader analysis area can be provided compared with the conventional method. Since the I-Dt transformation curve from $\phi=m\pi$ to $\phi=(m+1)\pi$ is relatively flat, difference due to different products or wafers can be eliminated. Therefore, the problem of uncertain successful detection rate in the conventional method due to amplitude variations can be solved. It then becomes possible to use the same rule to determine the analytical endpoint for different products.

5. Anti-noise capability is better compared with the conventional method, because noises are absorbed by the integral term. Furthermore, problems due to difference in signal levels between different polishing tables can also be solved.

From the above-mentioned description, it is understood that the I-Dt transformation curve having characteristics associated with a cosecant function as shown in FIG. 3. The curve can be obtained by integrating the intensity of the reflected light along the time axis, followed by being divided by the product of the derivative of the intensity of the reflected light and the polishing time. Since the transformed curve has salient peaks, the function itself reveals the sign of the slope, and the transformed curve are relatively flat between peaks, correct and stable rules can therefore be provided to determine the analytical endpoint. The problems encountered in conventional methods are therefore overcome. Note that the present invention not only detects the thickness of a dielectric layer in a CMP process, it can also be applied to optical devices based on the similar principles.

The method to inspecting the thickness of a material layer is described in the following paragraphs.

A material layer is polished, so that the thickness of the material layer decreases gradually as time goes by. During the polishing process, as incident light source, for example, a laser light is incident onto the material continuously. The incident light is then reflected from the top surface and the bottom surface of the material layer. The reflected light is collected and an intensity thereof is measured. The intensity I of the reflected light is integrated by time t, and differentiated by time t. The derivative of the intensity of the reflected light is denoted by I'. An I-t transformation, that is, an I-Dt relation is then derived as Eq. (3), and the I-Dt curve is drawn as FIG. 3.

It is shown that there are several obvious peaks 308, 312, 314, 316 of the I-Dt curve. Between the peaks 308 to 316, a flat curve indicates that the removal rate of the material layer is linear. The peaks 308 to 316 reflect a certain value of thickness of the material. The thickness of these peaks 308 to 316 can be derived from the relationship of $d_m$. Therefore, a real time thickness between any two peaks can be obtained. That is, the thickness values of the peaks 308 to 316 are calculated first. The thickness difference between two peaks 308 to 316 is obtained. The removing rate is then obtained by using the thickness difference divided by the time interval between two peaks 308 to 316. At any point between two peaks 308 to 316, the thickness of the point can thus be determined by deducting the thickness value of an earlier peak with the product of the removing rate and the time interval between the point and the earlier peak.

Referring to FIG. 3, the invention also provides a method of inspecting the endpoint of CMP process. While a material layer is polished by CMP, an incident light, for example, a laser light is incident onto the material continuously. The reflected lights of the incident light are collected and the intensity thereof is recorded. The intensity is then integrated and differentiated by time. The integration of the intensity is then divided by the product of the differential of the intensity and time, so that an I-Dt curve is obtained. The peaks 308 to 316 reflects characteristic thickness values of the material layer. That is, at these peaks 308 to 316, the parameter $\phi=m\pi$(m is a positive integer or zero). The thickness values of these peaks 308 to 306 can thus be calculated by $$d_m = \frac{m\lambda_0 \cos(\alpha_{ref})}{4n}.$$

One of the peaks 308 to 316 closest to an estimated endpoint of the material layer is selected. After reaching the endpoint, the material layer is further polished for a period of time $t_{over}$.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for determining a thickness of a material layer, wherein the thickness of the material being decreased with time, the method comprising:

continuously shining an incident light onto the material while performing a polishing step;

measuring a reflected light intensity I of the incident light;

integrating and differentiating the intensity of the reflected light with time;

obtaining an I-Dt curve by dividing the integration of the intensity of the reflected light by a product of the differential of the intensity of the reflected light and time, the curve comprising a plurality of peaks which reflect characteristic thickness values of the material layer;

obtaining each characteristic thickness value of the material layer using optical principle of reflection;

selecting two of the peaks to calculate a thickness difference between these two peaks, as well as to record a time interval between these two peaks; and calculating a removal rate between these two peaks by a linear relationship; and obtaining a real time thickness at a time point between these two peaks by deducting the thickness value of an earlier peak between these two peaks by a product of the removing rate and a time interval between the earlier peak and this time point.

2. The method of claim 1, wherein the intensity of the reflected light can be calculated by:

$$I = I_A + I_B + 2\sqrt{I_A I_B} \cos(\phi)$$

and $$\phi = \frac{4\pi n d}{\lambda_0 \cos(\alpha_{ref})}$$

wherein I is the intensity of the reflected light, $I_A$ and $I_B$ represent intensities of a first and a second reflected lights, n is the refractive index, d is a real time thickness of a time point, $\lambda_O$ is a wavelength of the incident light, and $\alpha_{ref}$ is the reflected angle.

3. The method of claim 2, wherein I-Dt transformation can be represented as:

$$\frac{\int I dt}{I' \cdot t} = -\frac{(I_A + I_B)}{2\sqrt{I_A \cdot I_B}} \csc(\phi) \frac{dt}{d\phi} - \frac{1}{t}\left(\frac{dt}{d\phi}\right)^2$$

wherein I' is differential of I.

4. The method of claim 2, wherein the peaks of the I-Dt transformation curve reflect $\phi = m\pi$ and have thickness values calculated by $$d_m = \frac{m\lambda_0 \cos(\alpha_{ref})}{4n},$$

wherein m is a positive integer or zero.

* * * * *